United States Patent
Wilkening et al.

(10) Patent No.: US 9,936,896 B2
(45) Date of Patent: Apr. 10, 2018

(54) ACTIVE SYSTEM AND METHOD FOR IMAGING WITH AN INTRA-PATIENT PROBE

(75) Inventors: Wilko Gerwin Wilkening, Mountain View, CA (US); Lex Garbini, El Granada, CA (US); Ricardo Espinosa, Mountain House, CA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 1023 days.

(21) Appl. No.: 13/349,035

(22) Filed: Jan. 12, 2012

(65) Prior Publication Data

US 2013/0184571 A1 Jul. 18, 2013

(51) Int. Cl.
| | |
|---|---|
| *A61B 5/05* | (2006.01) |
| *A61B 5/06* | (2006.01) |
| *A61B 6/12* | (2006.01) |
| *A61B 6/00* | (2006.01) |
| *A61B 8/12* | (2006.01) |
| *A61B 6/03* | (2006.01) |
| *A61B 8/08* | (2006.01) |
| *A61B 5/00* | (2006.01) |
| *A61B 5/055* | (2006.01) |
| *A61B 90/00* | (2016.01) |

(52) U.S. Cl.
CPC ............... *A61B 5/066* (2013.01); *A61B 6/12* (2013.01); *A61B 6/5235* (2013.01); *A61B 6/5247* (2013.01); *A61B 8/12* (2013.01); *A61B 90/39* (2016.02); *A61B 5/0066* (2013.01); *A61B 5/0073* (2013.01); *A61B 5/055* (2013.01); *A61B 6/032* (2013.01); *A61B 6/037* (2013.01); *A61B 8/0841* (2013.01); *A61B 2090/364* (2016.02); *A61B 2090/3945* (2016.02); *A61B 2090/3966* (2016.02)

(58) Field of Classification Search
None
See application file for complete search history.

(56) References Cited

U.S. PATENT DOCUMENTS

| | | | | |
|---|---|---|---|---|
| 5,771,895 | A | * | 6/1998 | Slager .......................... 600/462 |
| 5,855,553 | A | * | 1/1999 | Tajima .................. A61B 19/22 600/407 |
| 5,860,923 | A | * | 1/1999 | Lenker et al. ................ 600/433 |
| 7,505,808 | B2 | | 3/2009 | Anderson et al. |

(Continued)

OTHER PUBLICATIONS

CartoSound, brochure, "Image Integration Module with SoundStar Catheter," Biosense Webster, 2007.

*Primary Examiner* — James Kish

(57) ABSTRACT

Registration is provided for imaging with an intra-patient probe. The intra-patient probe is used for imaging or the imaging is, at least in part, of the intra-patient probe. Either approach for imaging with an intra-patient probe uses active transitions for registration. In one embodiment, one or more markers in the intra-patient probe are moveable relative to the intra-patient probe, allowing avoidance of occlusions and providing more reliable marker detection for registration. In another embodiment, a value of a parameter for imaging with at least one modality is changed so that acceptable or better registration with an image of another modality may be made. The imaging is repeated with differences, such as field-of-view or scale, allowing for registration for different types of modalities.

9 Claims, 2 Drawing Sheets

(56) References Cited

U.S. PATENT DOCUMENTS

| | | | |
|---|---|---|---|
| 7,780,601 B2 | 8/2010 | Guracar et al. | |
| 2003/0167052 A1* | 9/2003 | Lee .................. | A61M 25/0108 |
| | | | 604/529 |
| 2004/0019266 A1* | 1/2004 | Marciante ........ | A61B 17/22004 |
| | | | 600/407 |
| 2005/0256398 A1* | 11/2005 | Hastings ................ | A61B 34/73 |
| | | | 600/423 |
| 2007/0208252 A1* | 9/2007 | Makower ............. | A61B 5/6851 |
| | | | 600/424 |
| 2008/0119727 A1* | 5/2008 | Barbagli et al. .............. | 600/424 |

* cited by examiner

ACTIVE SYSTEM AND METHOD FOR IMAGING WITH AN INTRA-PATIENT PROBE

BACKGROUND

The present embodiments relate to imaging with an intra-patient probe.

In many cases, different imaging modalities are used simultaneously or consecutively on the same patient. Multiple modalities may be used where one modality is primarily used to guide the positioning of surgical tools while another modality is used to provide diagnostic images. Multiple modalities may be used to acquire different diagnostic information. Imaging modalities include optical, optical coherence tomography, magnetic resonance, computed tomography, ultrasound, x-ray, positron emission tomography, or single photon emission computed tomography. Different modalities visualize different properties of tissue or are available for different procedures. Some of the modalities may include a sensor or scanner in an intra-patient probe, such as optical, ultrasound or magnetic resonance modalities. Other modalities, such as ultrasound, computed tomography, magnetic resonance, or x-ray, may be used to detect an intra-patient probe.

For multi-modality imaging, the relative position of the regions represented by the corresponding images may be aligned or registered. To enable co-registration of images acquired by different imaging systems, the geometric relationship between the imaging systems is established. In some embodiments, the spatial relationship between the imaging systems and the object (e.g., the catheter) is established, such as where the imaging with the different systems is not simultaneous.

Various approaches are used to register the modalities for image alignment. Positions and orientation sensors may provide position and orientation of one imaging system in a coordinate system of another imaging system. However, position sensors are costly and not compatible with some imaging modalities.

In another approach for registration, markers attached to one imaging system may be imaged by the other imaging system in order to determine position and orientation of one imaging system in the coordinate system of the other imaging system. For example, radio opaque markers are provided in imaging catheters. Such markers may be used for tracking the imaging catheter in a fluoroscopic image. While finding the approximate position of the markers in the fluoroscopic imaging plane is a lesser problem, determining the rotation angles is challenging. One marker, bone or other structure may, at least partially, occlude another marker, making position determination difficult or impossible. Determining the position or depth along the X-ray beams is an error-prone measurement. The depth of the markers position along the X-ray beams may affect scaling, resulting in ambiguity.

In another approach to registration, images acquired by one imaging system may be matched to images acquired by the other imaging system. However, images from different modalities may be difficult to match due to differences.

BRIEF SUMMARY

By way of introduction, the preferred embodiments described below include methods, systems, and computer readable storage media for imaging with an intra-patient probe. The intra-patient probe is used for imaging (e.g., scanning from the probe) or the imaging is, at least in part, of the intra-patient probe while in the patient (e.g., scanning from external to the patient to image, in part, the probe). Either approach for imaging with an intra-patient probe uses active transitions for registration. In one embodiment, one or more markers in the intra-patient probe are moveable relative to the intra-patient probe, allowing avoidance of occlusions and providing more reliable marker detection for registration. In another embodiment, a value of a parameter for imaging with at least one modality is changed so that acceptable or better registration with an image of another modality may be made. The imaging is repeated with differences, such as field-of-view or scale, allowing for registration for different types of modalities. These embodiments are used alone or together.

In a first aspect, a system is provided for imaging with an intra-patient probe. An ultrasound element is in the intra-patient probe. A marker connects with the intra-patient probe. The marker is integrated in the intra-patient probe to be repositionable while the intra-patient probe is within a patient. An imaging modality is configured to sequentially scan a patient while the intra-patient probe is within the patient. The marker is at different locations relative to the ultrasound element for different scans of the sequential scans. A processor is configured to register an ultrasound image acquired with the ultrasound element with an image of the imaging modality as a function of the marker at the different locations.

In a second aspect, a method is provided for imaging with a catheter. A marker connected with an imaging catheter within a patient is spatially modulated. The marker is detected as a function of the spatial modulation of the marker. An image is obtained with the imaging catheter. The image is registered with another coordinate system as a function of a location of the detected marker.

In a third aspect, a system is provided for imaging with an intra-patient probe. An imaging source is in the intra-patient probe. A marker is moveable relative to the imaging source. The marker connects with the intra-patient probe and is visible to an external imaging modality.

In a fourth aspect, a non-transitory computer readable storage medium has stored therein data representing instructions executable by a programmed processor for imaging with a catheter. The storage medium includes instructions for scanning, with a first modality using the catheter, a patient as a function of a first value of a first parameter; scanning, with a second modality, a patient as a function of a second value of a second parameter; altering the first value, second value, or both the first and second values; repeating the scanning associated with the altered value; and registering data from the scanning with the first modality with data from the scanning with the second modality as a function of the scanning before and after the altering.

The present invention is defined by the following claims, and nothing in this section should be taken as a limitation on those claims. Further aspects and advantages of the invention are discussed below in conjunction with the preferred embodiments and may be later claimed independently or in combination.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

DETAILED DESCRIPTION OF THE DRAWINGS AND PRESENTLY PREFERRED EMBODIMENTS

Figure 1:
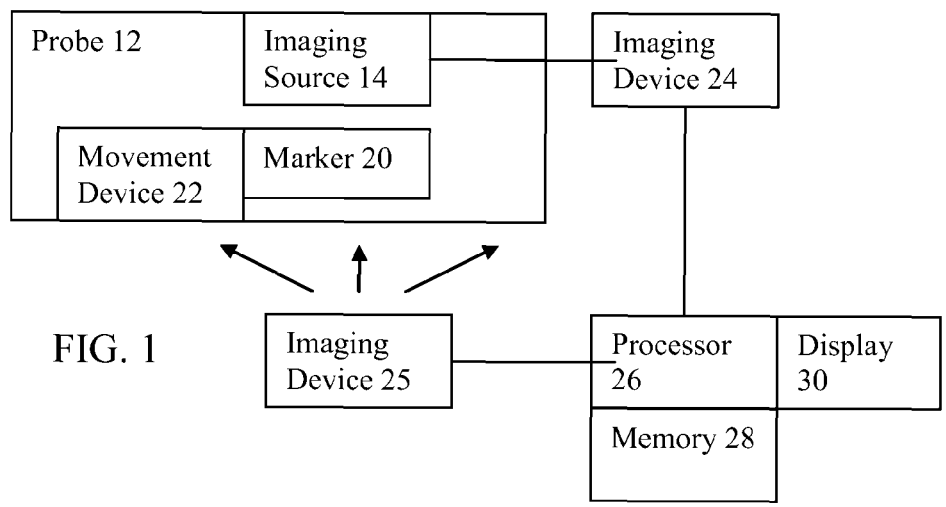
FIG. 1 is a block diagram of one embodiment of a multi-modality system for imaging with a intra-patient probe.

Marker-based and image-based registration include one or more imaging modalities with an intra-patient probe. The probe may be a catheter or a similar imaging sensor that cannot be positioned accurately by gears, levers, or shafts. Example intra-patient probes are intracardiac echocardiography (ICE) catheters, intravascular ultrasound (IVUS) catheters, optical coherence tomography (OCT) catheters, optical imaging catheters, and transesophageal echocardiogram (TEE) ultrasound transducers. The probe may not include an imaging sensor.

For marker-based registration, the space that is available for position markers in catheters or intra-patient probes may be very limited. The imaging system that observes the markers may not be able to derive enough information from the marker or set of markers for many reasons such as: the imaging system acquires two-dimensional projections (e.g. X-ray imaging) rather than three-dimensional images, suitable sets of markers do not fit into the space available, markers are partly masked by other structures, and contrast resolution or spatial resolution are not sufficient given the size of the markers. To assist in observation, the marker state (e.g., the size, position, orientation and/or pattern of a marker or set of markers) changes. The state change may follow a pre-defined pattern, or a certain state change may be requested by the system that identifies the markers to derive geometrical information. Because of the ability to change state, the markers may be referred to as active markers. By actively changing the position of a marker inside the catheter, marker-based registration may be enabled for a wider range of orientations and/or with higher accuracy. To determine the position and orientation of the catheter, the number of markers may be reduced. For example, one bigger marker that can be re-positioned may be better than three small, fixed markers. Any number of markers may be used.

For image-based registration, imaging parameters of one or more imaging systems are actively adjusted until reliable registration is achieved. In the case of the catheter-based imaging system, one important parameter is the orientation and focusing of the imaging sensor. The imaging system does not simply scan to form a three-dimensional image, but instead changes orientation, focusing, or other parameters based on feedback to enable co-registration. The orientation of the images acquired by the catheter or probe may be adjusted through feedback or controlled in a way that assists image-based co-registration.

Two embodiments are provided to assist registration. A marker inside or attached to an imaging catheter or probe may be repositioned or spatially modulated in a predictive manner or in response to an external signal. The orientation and size of the image from a probe or external imaging system may be changed through a feedback mechanism or in a predictable pattern such that the structure depicted in the resulting images may be matched to each other. The location of the probe may be more likely identified. These two approaches may be used separately. Alternatively, the two approaches are used together. Two independent registration determinations may be performed and then the results averaged or combined. The registration for one approach may use the results of registration using the other approach. The probe positioning may be used for generating three-dimensional ultrasound images.

FIG. 1 shows a system for imaging with an intra-patient probe 12. The system includes the probe 12, two or more imaging devices 24, 25, a processor 26, a memory 28, and a display 30. Additional, different, or fewer components may be provided. For example, another imaging device is provided. In another example, the probe 12 does not include an imaging source 14, marker 20, movement device 22, or is not itself included.

The processor 26, memory 28, and display 30 are part of a medical imaging system, such as one or both of the imaging devices 24, 25. In one embodiment, the processor 26, memory 28, and display 30 are part of the external imaging device 25. Alternatively, the processor 26, memory 28, and display 30 are part of an archival and/or image processing system, such as associated with a medical records database workstation or server. In other embodiments, the processor 26, memory 28, and display 30 are a personal computer, such as desktop or laptop, a workstation, a server, a network, or combinations thereof. The processor 26, memory 28, and display 30 may be provided without other components.

The probe 12 is for insertion into a patient. For example, the probe 12 is positioned in an orifice of the patient, such as through the mouth and into the esophagus. Alternatively, the probe 12 is positioned by surgical insertion through the skin of the patient, such as for minimally invasive surgery. In other embodiments, the probe 12 is inserted in an opening created as part of surgery, such as an inter-operative probe.

The probe 12 is an intra-operative probe, inter-cavity probe, catheter, needle, guide wire, or other medical device. In one embodiment, the probe 12 is any now known or later developed catheter for intervention or other use within a patient. The catheter is sized and shaped for use in the circulatory system, such as having a diameter of 10 French or less, but a length of a foot or more. Alternatively, the catheter is sized and shaped for use at other locations in the body. The catheter is adapted for insertion within the patient, such as through a vessel or vein for extending into a heart chamber, body cavity, or other location within the patient. The catheter may include guide wires or be inserted through another previously positioned guide catheter. The catheter may include an electrode, scalpel, balloon, stent, imaging array, tube for injection, or other device for treatment of the patient.

In one embodiment, the probe 12 includes an imaging source 14. The imaging source 14 is an array, sensor, lens, transducer, or other element for imaging or scanning the patient from the probe 12. For example, the imaging source 14 in the catheter is an ultrasound transducer element or array of an intracardiac echocardiography (ICE) catheter, is an ultrasound transducer element of an intravascular ultrasound (IVUS) catheter, is a lens or camera of an optical coherence tomography (OCT) catheter, is a lens or camera of an optical imaging catheter, or is an ultrasound transducer array of a transesophageal echocardiogram (TEE) ultrasound transducer. In alternative embodiments, the probe 12 is free of the imaging source 14.

The imaging device 24 is external to or within the probe 12. For example, the imaging device 24 is an ultrasound system with a beamformer, detector, and/or image processor connected to the imaging source 14 but positioned externally to the patient. The external ultrasound system connects with the imaging source 14 to scan. As another example, the imaging device 24 is a camera or video device for optical imaging. The camera or video connects with the imaging source 14 to view the patient from the probe 12. In yet another example, the imaging device 24 is an optical coherence imager. In another example, the imaging device 24 is a magnetic resonance (MR) system. The MR system connects with a local coil as the imaging source 14 in the probe 12. The imaging device 24 uses the imaging source 14 to view or scan the patient from the probe 12. Alternatively, the imaging device 24 is any modality for scanning a patient from an internal or external location, such as a magnetic resonance, computed tomography, positron emission tomography, or single photon emission tomography system.

As an ultrasound transducer element or array, the imaging source 14 may be used for scanning a one, two, or three-dimensional region of a patient from the probe 12. A piezoelectric or microelectromechanical (e.g., capacitive membrane ultrasound transducer) element or elements transduce between electrical and acoustic energies for scanning the patient. An array of such elements may be used to electronically scan or steer in two or three dimensions. A single element or an array of elements may be used to mechanically scan in one or two dimensions. For example, an element or elements connect with a drive shaft and are rotated within the probe 12. The rotation causes scanning with ultrasound of different locations around the probe 12. Other arrangements may be provided.

In one embodiment, the probe 12 includes one or more markers 20. The markers 20 are opaque to the scanning of the external imaging device 25. The markers 20 may be opaque or have other characteristics detectable in more than one imaging modality, such as being detectable by x-rays and magnetic resonance. In one embodiment, the markers 20 are metal objects. Tungsten or other material (e.g., other metals or barium sulfate) may be detected by x-ray or magnetic resonance scanning, such as fluoroscopy. The markers 20 are spherical, oblong, cuboid, cylindrical, conical, or other shape. The markers 20 are sized to fit within the probe 12, such as being 5 mm (e.g, in a TEE) or 2 mm (e.g., in a cardiac catheter) in radius or less. Larger or smaller markers may be used. Other materials may be used. In one embodiment, the markers 20 are particles suspended in a liquid. For example, magnetic particles are suspended. The particles may have any shape or density. In another embodiment, one of the markers is an acoustic array or transducer element (e.g., imaging source 14 itself). Where the imaging source 14 can be moved mechanically (e.g., moved for 3D imaging or for simple 2D scanning with a single element), the imaging source 14 may be a marker. In yet another embodiment, the marker 20 are light (e.g., blinking LEDs), radiation, acoustic, or other sources of energy. The marker 20 may appear to move by activation of different points or sources or may physically move.

Figure 2:
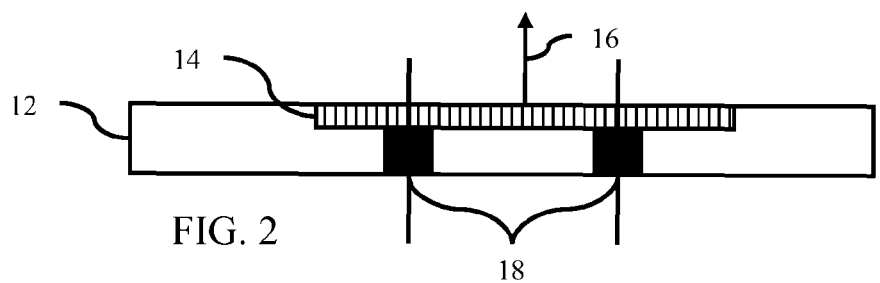
FIGS. 2 and 3 are illustrations of spatial modulation of a marker in a catheter.

One or more markers 20 are provided. The markers 20 are located within the probe 12 adjacent to the imaging source 14. For example, three markers are positioned adjacent to the imaging source 14. FIG. 2 shows two possible markers 18 positioned adjacent to the backing or back-side of an ultrasound array used as the imaging source 14. The acoustic scanning generally is performed along a vector 16 extending from the face of the imaging source 14. "Generally" is used to account for steering at non-orthogonal angles, such as over a 120 degree field of view. The markers 20 are positioned along a longitudinal axis of the probe 12, but may be spaced at different distances relative to the longitudinal axis of the probe 12 to define a plane. The markers 20 are positioned along a common or same generally rigid or rigid portion of the probe 12. Generally rigid indicates more rigidity than other portions of the probe 12 to be inserted within the patient. By using three or more markers 12, a position and orientation within three-dimensions or a volume of the scan vector 16 or scan plane may be detected. Alternatively, fewer markers (e.g., even a single marker) may be shaped to detect position and orientation (e.g., a cone shaped single marker may indicate orientation and position). Additional markers 20 may provide redundancy and/or more information for improved accuracy. Other markers 20, with or without a same shape or size, may be positioned elsewhere on the probe 12.

The markers 20 connect with the probe 12. The connection may be fixed, such as connected with a set orientation to a drive shaft. The connection may be flexible, such as connected through elastic or flexible material to the probe 12. The connection may be guided, such as placement within a liquid, gas, or vacuum filled tube or as placement along a rail or other guide.

The connection allows for repositioning of the marker 20 while the catheter is within a patient. One, fewer than all, or all of the markers 20 adjacent the imaging source 14 and/or within the probe 12 are repositionable relative to the probe 12 and/or imaging source 14. One or more markers 20 may be connected in a fixed manner relative to the probe 12 and/or the imaging source 14. By connection allowing for repositioning, the marker 20 may be moveable relative to the imaging source 14 and/or probe 12 during use of the probe 12 within the patient.

The repositionable connection is provided by fluid, flexible, or fixed connection. For a fixed connection, the marker 20 is fixed to a movable object, such as the drive shaft. The probe 12 includes a guide, volume, or other space for allowing movement. Blocks or other restrictions for the movement may be included. Different types of connections may be provided depending on the type of movement device 22.

The movement device 22 connects with one or more markers 20. Separate movement devices 22 may be provided for each repositionable marker 20. The connection is direct (e.g., drive shaft connected with the marker 20) or indirect (e.g., applying magnetic, acoustic or other force to move the marker 20).

In one embodiment, the movement device 22 is an electromagnet. A coil or other conductor is positioned within the probe 12 and near the marker 20. By activating the electromagnet, the marker 20 is attracted or repelled. A bias source, such as a spring or gravity, may be used to reposition when the electromagnet is not activated. Alternatively, the polarity of the electromagnet is switched or another electromagnet is provided at a different location. The marker 20 may be particles or an object positioned in a chamber, such as particles in a fluid filled chamber. The electromagnet is positioned adjacent to the chamber. For particles, the spatial particle density may be modulated or altered for different locations by a variable electromagnetic field. The magnetic field may be used to change the marker contrast, for example by magnetic emulsion. The direction of elongated particles may be controlled, providing for different levels of opacity based on direction. Magnetic particles are alternatively moved by a magnet external to the patient. The liquid and particles are in a channel so that the movement of the particles is guided. The particles move to a location that is defined with respect to the coordinate system of the catheter by the channel in response to the external magnetic force.

In another embodiment, an ultrasonic motor or an actuator connects with or adjacent to the marker 20. An ultrasonic motor uses acoustic energy to move the marker 20 or device connected with the marker 20. A hydraulic or pneumatic system may alternatively move the marker 20. Using change in fluid or gas pressure, the marker 20 may be moved. In another alternative, the movement device 22 is external to the patient, such as a source of acoustic energy sufficient to move the marker 20. The acoustic radiation force is transmitted to the marker 20 to cause movement of the marker. Vibration or other forces may be used.

In yet another embodiment, the movement device 22 is a drive shaft used for scanning with the imaging source 14 or steering the probe 12. For example, one or more markers are mounted on a drive shaft of a mechanically scanning IVUS catheter. A drive shaft just for the marker 20 may be provided in other embodiments. An electronic or other motor positioned outside the patient operates the drive shaft to move the marker 20. The marker 20 is rotated and/or translated by the drive shaft. In other embodiments, a control wire or steering wire connects with the marker 20 for manual or automated movement of the marker 20.

In one embodiment, the movement device 22 is a memory metal object connected with the marker 20. Nickel Titanium, bimetal, or other structures dispose the marker 20 at one location, and then dispose the marker 20 at another location when activated. Electrical or temperature changes may activate the memory metal. For example, an electric coil or other heating element causes the memory metal to expand, contract, bend, or change shape, moving the marker 20. The marker 20 is moved laterally, translated, expanded, and/or rotated.

By providing for movement of one or more markers 20, the number of markers 20 may be reduced. Each marker 20 may be more reliably located, so less redundancy may be needed. Fewer markers 20 may allow the markers 20 to be larger or have greater spatial separation, further increasing the detectability. Moveable markers 20 may avoid or prevent overlap between markers 20. Fewer markers 20 may result in less overlap. Where overlap does occur, the change in position of the markers 20 may allow identification even with overlap.

The movement device 22 operates automatically or in response to control by the processor 26 or other controller. Alternatively, the movement device 22 operates in response to user activation. The user activates the movement device 22 by selection on a user interface. Alternatively, the user controls the movement by hand, such as by a trigger or other device for moving a control wire.

The movement device 22 operates continuously, periodically, when triggered, or in response to an event. For example, the markers 20 are moved in a periodic pattern or at intervals. The pattern is defined in the spatial domain (where the markers move) and/or in the temporal domain (when and how fast they move). All of the markers 20 move with the same pattern. Alternatively, different markers 20 may move based on different patterns, such as by moving different amounts, different speeds, different periods, different directions, different types (e.g., rotational verses lateral), or other differences. The different patterns may be used to identify one marker 20 from other markers 20.

Feedback may be used to control movement of the markers 20. For example, the markers 20 are kept in one position. After scanning, the user or a processor may indicate possible overlap or ambiguity in identifying the markers 20 in the scan data. One or more markers 20 are moved in response to this feedback. For example, one marker 20 overlaps with another marker 20 relative to a scan by the external imaging device 25. Where fewer than all the markers 20 are detected or the markers 20 are detected as overlapping, this feedback is used to move one or more markers 20. As another example, one or more markers 20 are obscured, such as by bone, probe structure, or implant. Where fewer than all the markers are detected, this feedback is used to move one or more markers 20. If all of the markers 20 are detected without ambiguity, the markers 20 may not be moved.

Using feedback that changes marker position may enable or improve the quality of the co-registration. Feedback may be in response to recognition that the markers 20 are overlapping so that one or more markers 20 are moved to eliminate the overlap. Feedback may be in response to recognition that one or more markers 20 are obscured by structures within the catheter or other objects internal or external to the catheter so that one or more markers 20 are moved to improve visibility of the previously obscured marker 20.

The external imaging device 25 is a magnetic resonance, computed tomography, positron emission tomography, single photon emission tomography system, ultrasound, x-ray, fluoroscopy, optical, or other imaging modality. The external imaging device 25 is located externally to the patient. Sensors or elements may be spaced from the patient or positioned against the patient. The sensors or elements are used to scan a one, two, or three-dimensional region of the patient. Data representing specific locations may be acquired. Alternatively, projection data (e.g., x-ray) may be acquired.

The external imaging device 25 sequentially scans the patient while the probe 12 is within the patient. The sequence of scans may be of the same or different locations. For example, a two or three-dimensional scan of the same plane or volume is repeated. The repetition is triggered, such as in response to feedback indicating ambiguity in determining marker position, or is periodic, such as scanning in a continuous or on-going manner.

Figure 3:
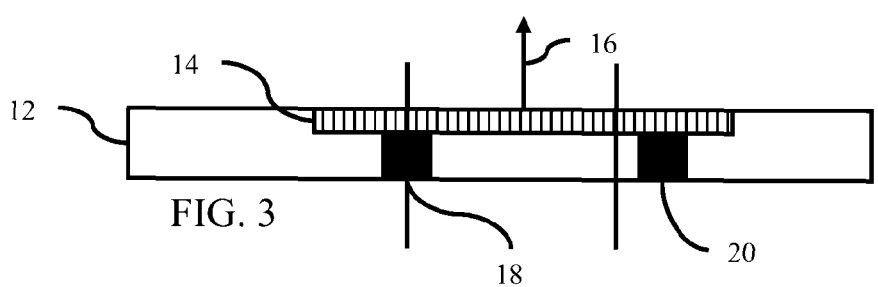

One or more markers 20 are at different positions for different scans. For example, FIG. 2 shows two possible markers 18 adjacent to an array of elements as the imaging source 14. To distinguish between other structures and the marker 20, the marker 20 is moved. FIG. 3 shows the marker 20 moved relative to the imaging source 14 and the probe 12 without movement of the imaging source 14 and the probe 12. The possible marker 18 on the right is identified as being the actual marker 20. The other possible marker 18 may be a non-moved marker 20 or may be identified as not a marker due to lack of movement. The sequence of scans allows distinguishing between markers 20 and other objects.

The processor 26 is a general processor, central processing unit, control processor, graphics processor, digital signal processor, three-dimensional rendering processor, image processor, application specific integrated circuit, field programmable gate array, digital circuit, analog circuit, combinations thereof, or other now known or later developed device for controlling the movement device 22, controlling the imaging devices 25 and/or 24, registering the coordinate systems of the imaging devices 24, 25, and/or generating displays. The processor 26 is a single device or multiple devices operating in serial, parallel, or separately. The processor 26 may be a main processor of a computer, such as a laptop or desktop computer, or may be a processor for handling some tasks in a larger system, such as being part of the imaging devices 24 or 25. The processor 26 is configured by instructions, design, hardware, and/or software to perform the acts discussed herein, such as registration.

The processor 26 is configured to control the movement device 22. The processor 26 identifies markers. Any marker identification may be used, such as thresholding or pattern matching. The pattern matching may be of a movement or change pattern for a given marker 20 and/or of relative positions of a plurality of markers given change by one or more markers 20. Alternatively, user input is received by the processor 26 for indicating markers. The processor 26 determines whether sufficient markers 20 are identified or whether there is ambiguity. For example, the marker identification may use a probabilistic approach where markers 20 are identified with a probability of correct identification. Where markers 20 have a probability below a threshold, even if the correct number of markers 20 is identified, the processor 26 may control the movement device 22 to resolve the ambiguity. If markers 20 overlap with other structures or markers 20, moving the markers 20 in a predictable pattern may enable reliable detection (e.g., the marker locations are locked in using pattern recognition or determining the structure from motion).

The processor 26 controls the imaging devices 24, 25 to acquire scan data. The external imaging device 25 is controlled to acquire data representing an internal region of the patient and the markers 20. The processor 26 may cause the external imaging device 25 to repeat a scan in response to movement or after movement of one or more markers 20. Based on the feedback from the scanning, the movement of the markers 20 and the repetition in scanning are controlled. The markers 20 associated with expected movement, change in position, or location may be identified from a repeated scan. The markers 20 may be detected with less or no ambiguity due to the spatial difference.

The imaging device 24 is controlled to acquire data for registration or display. Similarly, the processor 26 may generate an image or cause display of an image from the external imaging device 25 for diagnosis and/or probe 12 positioning.

The processor 26 registers the coordinate systems and corresponding images. If imaging with both (or more) imaging systems is performed simultaneously or during a same examination, the relationship between the coordinate systems of the imaging systems is found using the markers. If the imaging is done consecutively (e.g., not on the same day), landmarks or fiducial markers may be identified in addition to the use of the markers.

By detecting the positions of the markers 20 without ambiguity, a location and/or orientation of the imaging source 14 within the patient may be detected. The location and orientation may be used to determine a location of a scan line, plane or volume from the imaging source 14 relative to the coordinate system of the external imaging device 25. The position of the imaging source 14 relative to the markers 20 is known or approximated for transforming coordinates between the imaging devices 24, 25.

Using the marker positions, the scanning and corresponding data or images of the different imaging devices 24, 25 are registered. The relative coordinate systems are aligned through interpolation, extrapolation, matrix, and/or other transform function. For example, an ultrasound image acquired by an ultrasound element or array of the probe 12 is registered with an image from the external imaging device 25 using the marker locations. The marker locations in the image from the external imaging device 25 indicate the relative location of the probe 12 and array of the imaging source 14. The array location indicates the scan plane or region for the image from the imaging device 24.

The processor 26 alternatively or additionally causes changes in the scanning by one or more imaging devices 24, 25. The registration may be based on correlation of images or data with or without also performing marker detection. For example, the processor 26 searches through different relative translations and rotations between data from scans by the different imaging devices 24, 25. Minimum sum of absolute differences, correlation, or other similarity measures are calculated for each relative position. The translation, scale, and/or orientation with the greatest similarity indicate the correct registration. Different results may be obtained using at least one different value of a scan parameter. The processor 26 controls the scanning to vary the value of the parameter until a better, sufficient, or desired match is achieved. For example, the best alignment may yield a correlation below a threshold. The scanning is varied by the processor 26 until the best alignment has a correlation above or at the threshold. Alternatively, the scanning is varied to provide a list of best registrations—one for each value of the parameter. The registration with the greatest similarity is selected.

The memory 28 is a graphics processing memory, a video random access memory, a random access memory, system memory, random access memory, cache memory, hard drive, optical media, magnetic media, flash drive, buffer, database, combinations thereof, or other now known or later developed memory device for storing data or video information. The memory 28 is part of an imaging system, part of a computer associated with the processor 26, part of a database, part of another system, a picture archival memory, or a standalone device.

The memory 28 stores scan or image data for registration and control data for controlling the movement device 22 and/or imaging devices 24, 25. The memory 12 stores the models or templates for various patterns associated with one or more markers.

The memory 12 or other memory is alternatively or additionally a computer readable storage medium storing data representing instructions executable by the programmed processor 26 for imaging with an intra-patient probe. The instructions for implementing the processes, methods and/or techniques discussed herein are provided on non-transitory computer-readable storage media or memories, such as a cache, buffer, RAM, removable media, hard drive or other computer readable storage media. Non-transitory computer readable storage media include various types of volatile and nonvolatile storage media. The functions, acts or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code and the like, operating alone, or in combination. Likewise, processing strategies may include multiprocessing, multitasking, parallel processing, and the like.

In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU, or system.

The display 30 is a monitor, LCD, projector, plasma display, CRT, printer, or other now known or later developed devise for outputting visual information. The display receives images, graphics, or other information from the processor 26 or memory 28.

One or more images representing the probe position relative to a patient region are displayed. The image may be of a position, such as displaying coordinates. The image may be of a medical scan representing the region of the patient. For example, the position information is overlaid as a graphic on an image or images representing the patient. The position of the medical device is highlighted, marked by a graphic, or otherwise indicated on the image.

The position may be used for purposes other than display. For example, the location is used to register a position of an image plane relative to a volume. As another example, the position is used for planning. The direction of travel of an interventional device is determined and instructions are provided to avoid tissues or organs.

Images from both imaging devices 24 and 25 may be displayed. Separate images are displayed. The spatial relationship of one image to another may be displayed as well, such as using a graphic overlay, indicating the position of the probe 12, or providing an icon showing the relative positions of the scan regions. One rendering from data from both imaging devices may be generated. The data may be coded differently (e.g., gray scale for fluoroscopy and color for ultrasound or vise versa) to distinguish the data from the different sources in the rendered image.

Figure 4:
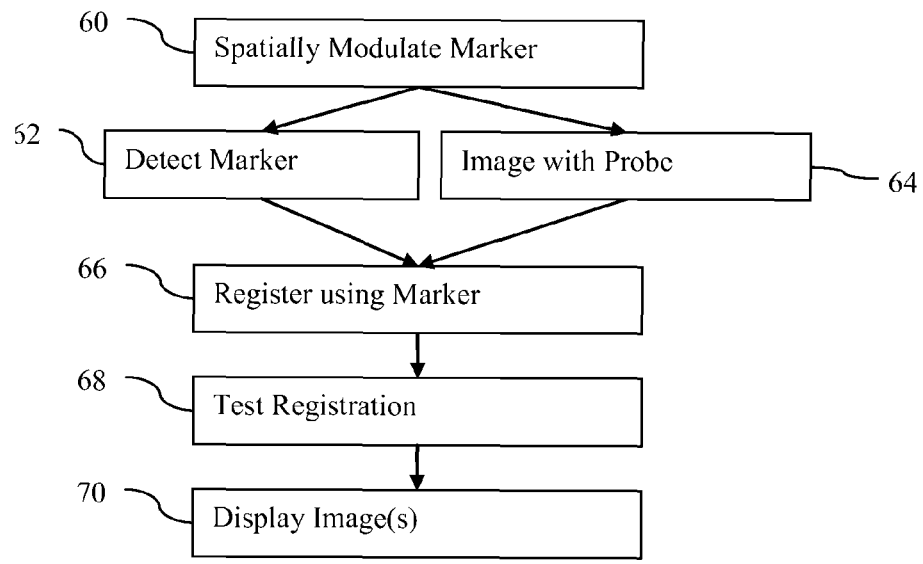
FIG. 4 is a flow chart diagram of one embodiment of a method for registering images from different modalities using a spatially repositioned marker.

FIG. 4 shows one embodiment of a method for imaging with an intra-patient probe, such as a catheter. In this embodiment, the imaging is with the probe by using the probe is to generate one or more images. The method is performed by the system of FIG. 1 or a different system. The acts are performed in the order shown, but other orders may be provided. For example, act 60 is performed after acts 62 and 64 and based on feedback from acts 62 and/or act 68. Additional, different, or fewer acts may be provided. For example, the test of registration in act 68 is not performed. Instead, the detection of markers is tested for determining whether to modulate the marker in act 60. As another example, the modulation of the marker in act 60 occurs without any testing, such as without the testing of act 68 or testing for marker detection.

In act 60, one or more markers are spatially modulated. Alternatively, one or more, such as all but one, of the markers are fixed in position relative to a probe. Any number of markers may be provided. The discussion below will be for one marker, but applies to other markers as well.

The marker connects with a probe inserted into a patient. The connection allows for movement or change of the marker. The marker changes position, orientation, shape, and/or size. The change is by lateral movement, rotational movement, expansion, or other alteration.

The spatial modulation is a single change, such as moving the marker from one position to another as shown in the transition between FIGS. 2 and 3. The spatial modulation may repeat, such as movement back and forth. The spatial modulation may be periodic or on-going, such as providing for change every 1-3 seconds or constantly moving other than at the time of direction reversal. The spatial modulation may be in a repeating pattern that is predetermined. The expected pattern may be detected based, at least in part, on an imaged object following the pattern. Alternatively, the spatial modulation is performed in response to and/or with a pattern established by user activation or other trigger not known prior to use.

The spatial modulation of one marker may be based or performed in correspondence with spatial modulation of one or more other markers. The markers move in common, at different times, at different rates, by different amounts, at different frequencies, or with other differences. The pattern established by multiple markers may be identified to better distinguish each marker from other material. Alternatively, each marker is spatially modulated independently of or without regard to the modulation of other markers.

The spatial modulation is performed for initial detection of the markers. The detection in act 62 is performed based on multiple scans of the same locations to identify the markers. Alternatively, the markers are maintained in a same position (e.g., spatial modulation is not initially used) until there is an indication of poor detection or poor registration. The spatial modulation is performed in response to a result of the testing in act 68 or testing after the detection in act 62. If the registration is not sufficient or has an undesired level of ambiguity, the modulation of act 60 is performed and the detection of act 62 is repeated.

In act 62, the marker is detected. In an initial detection, the marker is detected based on being opaque to an external scan modality. For example, the marker is metal. Fluoroscopy, x-ray, or other radiation is transmitted to image a region of the patient. The marker causes an artifact or is otherwise detectable from the scan. Alternatively, the initial detection relies on spatial modulation of the opaque marker.

Any now known or later developed detection may be performed. Thresholding (intensity, shape, size . . . ), region growing, filtering, template matching, and/or other processing are performed to identify the marker. The detection may use multiple markers. For example, a machine-learnt matrix finds a plurality of markers based on training data. As another example, known spatial relationships between markers are used to select possible markers as the markers.

In later repetitions or initially, the marker may be detected based, at least in part, on the spatial modulation. Multiple scans of the patient are performed. Differences between the data from different scans are identified. For example, data resulting from one scan is subtracted from data resulting from another scan. A threshold is applied to isolate or segment substantial differences. Where the differences represent a change in position or other spatial modulation associated with the marker, the marker is identified. Other approaches using spatial modulation may be used. For example, the difference is one of a plurality of features used to detect the marker. The difference and other information (e.g., features derived from one or multiple scans, such as Haar features or steerable features) are input to a matrix to detect the markers. Alternatively, markers are detected individually or as a group in both sets of data, and, then, comparison is made to further distinguish the markers based on spatial modulation.

Instead of detecting based on the difference, the detection of the marker due to spatial modulation may be based on positioning to a less ambiguous location. Where a marker is obscured by other structures (e.g., other markers, probe structure, or anatomy), the spatial modulation may result in more reliable detection of the marker in a given scan. The movement positions the marker away from the obstruction. Marker detection based on features of the marker other than the modulation may be used to detect the marker from data of a scan after the modulation. The marker is separably detectable due to movement away from the obstruction.

The detection of the marker may be tested. If an insufficient number of markers or too many markers are identified, there is ambiguity in the marker detection. If the marker has an unexpected shape, size, or orientation, there may be ambiguity in the marker detection. If the marker has an unexpected position, there may be ambiguity in the marker detection. Where the detection is probabilistic, a probability of the marker being correctly identified may be below a threshold, indicating ambiguity.

Where there is ambiguity, the marker is spatially modulated in act 60 and the detection of the marker is repeated in act 62. The repetition uses the spatial modulation to redetect the marker. In alternative embodiments, the testing is not performed but spatial modulation is used to provide increased accuracy as compared to not using spatial modulation and corresponding detection.

In act 64, an image is obtained from a probe. For example, an optical, ultrasound or MR scan is performed using the probe. A sequence of images may be obtained. The patient is scanned from the probe while the probe is within the patient. The scan is of a one, two, or three-dimensional region of the patient adjacent to the probe. The scanned region is defined by the scanning, such as a sector, Vector®, or circular plane sampled based on scan line density, scan line spacing, and sampling timing in ultrasound. The data represents locations defined by the scanning system. The data is used to generate an image for diagnosis.

Another image is acquired for the detection of act 62 or separate from the detection. The other image is from a different modality. For example, ultrasound is used for act 64 and fluoroscopy or x-ray is used for act 62. The ultrasound image is used to guide placement of the probe, a separate catheter, and/or diagnosis. The fluoroscopy image is used for guiding placement of the probe and/or diagnosis. Since different scanning systems are used, the spatial relationship between the images is not known.

To establish the spatial relationship, the images (e.g., data to be used to form the images) are registered in act 66. The registration is performed, at least in part, based on the detected markers. The markers are detected in one image. The markers have a known spatial relationship with the probe and sensor or array for scanning from the probe. For example, the markers are positioned to indicate a plane corresponding to a scan plane of an ultrasound array. The markers are at particular distances from the array. Using the markers, the scan plane of the ultrasound image is spatially registered relative to the fluoroscopy image. The relative scale may be determined by the spacing of the markers. Any marker-based registration may be used.

The registration aligns coordinate systems between the different scanning systems or imaging modalities. The image from one system may be registered with an image from another system by spatial alignment. Other registration may be provided, such as transforming spatial coordinates from one system with the other system based on the spatial relationship. Yet another registration may be provided by interpolation, extrapolation or other conversion of data from one system to the coordinates of the other system or a common grid. Any type of registration may be provided.

In act 68, the registration is tested. The data from the different systems may be correlated as aligned. Any similarity measure may be used, such as minimum sum of absolute differences or cross-correlation. If the similarity is below a threshold, the registration fails the test. Other testing may be used. For example, the registration itself may fail. As another example, there may be multiple different registrations with a similar confidence or range of similarity, creating ambiguity.

If the testing fails, act 60 may be performed and the detection in act 62 and registration in act 66 repeated. The testing in act 68 may be repeated as well. If the registration passes the testing, the registered data is used for display.

In act 70, one or more images are displayed. The images from the separate systems may be separately displayed. The separate display may be sequential or simultaneous. For example, images from each modality are displayed adjacent to each other.

The registration may be used to indicate a location for a graphic overlay on one of the images. The graphic overlay indicates a position of one of the images relative to the other. Graphic overlays may be provided for one or both images. In an alternative embodiment, an icon, separate wire frame or other illustration is used to show the relative position of the images or scan region. The icon or separate wire frame is spaced from the image or images. In yet other embodiments, the registered data is used together for rendering an image. One image is formed from both types of data. The different data may be distinguished by color, brightness, or other characteristic. Where one set of data represents three-dimensions, an image may be rendered using both types of data and the relative positions, orientation, and scale indicated by the registration.

Figure 5:
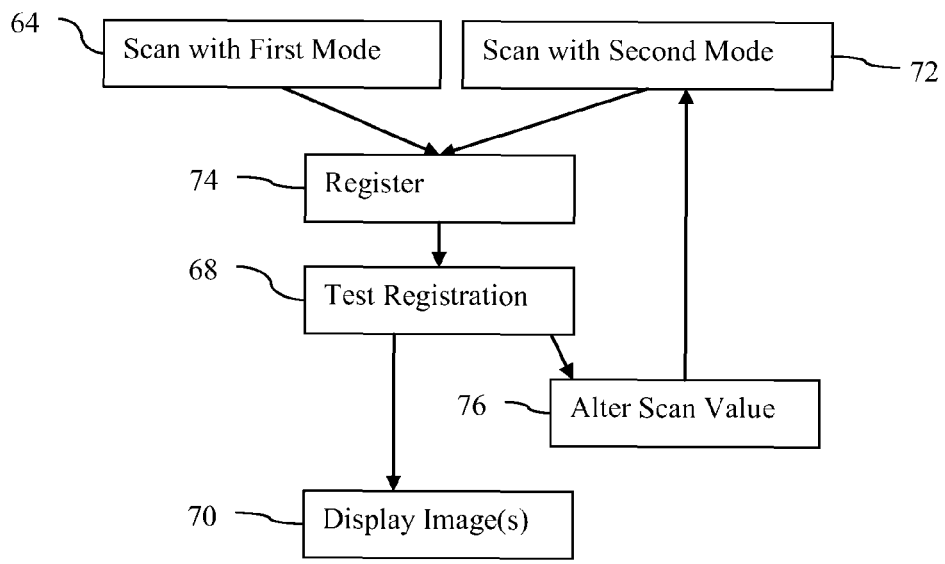
FIG. 5 is a flow chart diagram of one embodiment of a method for registering images form different modalities using scan value alteration.

FIG. 4 is directed to marker-based registration. As an alternative or additional registration, data or image-based registration may be used. FIG. 5 shows one embodiment of a method for image-based registration. Data from different modalities is registered. The registration may be difficult due to the differences in the modalities. Imaging modalities that use X-rays, for example, are well suited for imaging bones while the soft-tissue contrast is very low. Ultrasound provides good contrast between tissue types, but hardly penetrates bones. Certain types of features may be detected by one modality only. Due to these differences, comparison of data or images may be difficult. The registration is made more difficult by differences in dimensionality, size, orientation or scale. Even using processing to have one type of data emulate another type of data for registration, these differences may result in poor registration.

FIG. 5 shows the use of feedback for rescanning with a different setting. This feedback may result in sufficient or better registration. The method of FIG. 5 is implemented by the system of FIG. 1 (e.g., with or without the imaging source 14, the marker 20, and/or the movement device 22) or a different system. One or both imaging modalities may use scanning from within or external to the patient. For example, a probe is inserted into a patient for imaging from the probe. Another modality is used to image the probe. As another example, both modalities are external to the patient. Any probe may or may not be imaged by one or both modalities.

The acts of FIG. 5 are performed in the order shown or a different order. As shown, acts 64 and 72 are performed in parallel. Sequential performance may be used. Additional, different, or fewer acts may be provided. For example, act 76 is not performed where the test of act 68 indicates sufficient registration. As another example, testing act 68 is not performed where the alteration of act 76 automatically provides options for registration.

In act 64, a patient is scanned with one modality. For example, the patient is scanned by ultrasound from a catheter or other probe within a patient or from a probe on the skin of a patient. The scan is from within the patient or from external to the patient.

The scan is performed as a function of settings. Parameters may be set by corresponding values. For example, the scan line density, sampling density, steering angles, scan format, number of scan lines, aperture size, apodization, focusing profile, beam width, frequency, waveform (e.g., number of cycles or type of wave), and/or other parameters are assigned values. Depending on the settings, different orientations, fields of view, types of data detected, resolutions, scale, or other characteristics of the scan are provided. Other settings may be used for other types of modalities. For example, the energy level, collimation, angle of incidence, repetition frequency or other settings are provided for fluoroscopy or x-ray. Gradient, pulse sequence, coil selection, or other settings are provided for magnetic resonance.

In act 72, the patient is scanned with another modality. The other modality uses the same or different system. For example, a combined PET/CT or PET/MR system is used to scan with different modalities. The scanning is simultaneous or sequential with the scanning of act 64. Like act 64, the scanning is performed based on settings for one or more parameters.

The same general region of the patient is scanned. Different sized, shaped, oriented, or sampling density regions may be provided for the different scans in acts 64 and 72.

In act 74, the data from the different scans is registered. The image data being registered is data formatted for display as an image, intensity data, or other image data not yet displayed as an image. Alternatively, the data being registered is of previously displayed images. The data may be processed prior to registration, such as converting data from one mode to emulate data from the other mode. For example, noise emulating speckle patterns is added to fluoroscopy data. Alternatively, directional edge detection is performed to identify interfaces detectable with ultrasound.

The registration is based on similarity. The data from the different scans are relatively translated, oriented, and/or scaled. For each relative change, the similarity is measured, such as using correlation or absolute differences. Any search pattern may be used, such as testing every possibility, using a data pyramid to progressively register at different resolution, setting step size based on level of similarity, setting step direction based on increasing or decreasing similarity, registering rotation after translation, or other process. The relative position (location, orientation and/or scale) with the greatest similarity is identified. The greatest similarity may indicate the registration or alignment of the scans. Other registration techniques may be used, such as machine-learning based registration.

In act 68, the registration is tested. If sufficient registration is provided, act 70 is performed. If insufficient registration is provided, act 76 is performed. Alternatively, act 76 is performed automatically and the test for registration is a selection of a greater correlation from repetitions of act 74 responsive to different settings.

In act 76, one or more values are altered. One or more values for one modality and not the other are altered. Alternatively, values for both modalities are altered.

The alteration is in a predetermined pattern. The pattern may be based on the types of modalities being registered. Common or typical differences between given modalities may be used to determine the adjustment. Which parameter to change and by how much may be based on the types of modalities. The change may be based, at least in part, on the registration. The amount of change may be a function of the level of similarity obtained. The number of parameters to change at one time may be a function of the level of similarity obtained. Higher similarity may indicate a smaller change in the value.

The repetition of scanning, registration, and alteration may occur multiple times. The pattern of alteration may be based on a single change or a plurality of changes. The alteration may adapt to previous registrations. For example, where the registration becomes worse, the value may be altered in a different direction (e.g., increased instead of decreased again). Where the alteration does not yield sufficient results, different parameters or combinations of parameters may be selected for alteration.

The alteration may be based on detected artifacts. As an alternative or in addition to testing the registration, the scan data is tested. Where the data includes artifacts or other characteristics making registration more likely to fail, a value for one or more parameters associated with the characteristic is altered. In other embodiments, information about the object being scanned may be extracted from data of one scan. The information is used to alter a value of a parameter for a repeated scan by the same modality or the scan by the other modality. For example, the steering angle may be changed for ultrasound scanning where bone is indicated in a fluoroscopy scan.

The feedback-based system changes imaging parameters of one or both imaging systems to improve the quality of the co-registration. In one embodiment, the parameters establishing the field of view, scaling, and/or viewing angle are adjusted.

After alteration, the scanning of act 64 and/or 72 is repeated. The alteration is to one modality, but may be for both modalities. The scanning is repeated with the different or altered value. The resulting data is registered in act 74. The registration is tested in act 68. Further alteration may or may not be performed.

The repeated registration may use the same data from one of the modalities as the previous registration. Alternatively, both scans of acts 64 and 72 are repeated even though one of the scans may be repeated with the same settings.

Once a sufficient registration or a best registration from determined options is identified, one or more images are displayed in act 70. The images rely on or incorporate the registration.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

We claim:

1. A system for imaging with an intra-patient catheter, the system comprising:
    an ultrasound element in a catheter;
    a marker connected with the catheter at a portion of the catheter, wherein the marker is integrated in the catheter to be repositionable relative to the portion of the catheter while the catheter is within a patient;
    an imaging modality configured to sequentially scan a patient while the catheter is within the patient, the marker being repositioned at different locations relative to the ultrasound element between different scans of the sequential scans; and
    a processor configured to register an ultrasound image acquired with the ultrasound element with an image of the imaging modality as a function of the marker being repositioned at the different locations relative to the ultrasound element.

2. The system of claim 1 further comprising a linear array of elements in the catheter wherein the ultrasound element comprises an element of the linear array of elements and wherein the imaging modality comprises a fluoroscopy or x-ray modality.

3. The system of claim 1 wherein the marker comprises magnetic particles suspended in a liquid and further comprising an electromagnet.

4. The system of claim 1 wherein the marker comprises a radio-opaque object within a tube comprising the portion of the catheter in the catheter and further comprising an electromagnet, ultrasonic motor, or an actuator connected with or adjacent to the radio-opaque object.

5. The system of claim 1 wherein the ultrasound element connects with a drive shaft for mechanical scanning by the ultrasound element, the marker also connecting with the drive shaft for repositioning of the marker.

6. The system of claim 1 further comprising a memory metal object connected with the marker, the marker repositionable by operation of the activation of the memory metal.

7. The system of claim 1 further comprising a control wire connected with the marker, the control wire configured to reposition the marker.

8. The system of claim 1 further comprising a movement device configured to reposition the marker based on feedback received from the processor based on at least one of the scans by the imaging modality.

9. The system of claim 8 wherein the feedback is in response to the marker overlapping with another marker relative to the imaging modality or the marker being obscured.

* * * * *